United States Patent [19]
Hellenkamp et al.

[11] Patent Number: 5,246,259
[45] Date of Patent: Sep. 21, 1993

[54] APPLICATOR DEVICE FOR POSITIONING A CONTACT LENS ON THE HUMAN EYE

[76] Inventors: Johann Hellenkamp; Irma Hellenkamp; Brigitta Hellenkamp, all of 7790 NW. 55th St., Miami, Fla. 33166

[21] Appl. No.: 838,936
[22] Filed: Feb. 21, 1992
[51] Int. Cl.⁵ .................................................. A61F 9/00
[52] U.S. Cl. .................................... 294/1.2; 206/5.1
[58] Field of Search ........................... 294/1.2; 206/5.1; 606/107

[56] References Cited

U.S. PATENT DOCUMENTS

| | | | |
|---|---|---|---|
| 2,924,481 | 2/1960 | Wagstaff | 294/1.2 X |
| 3,063,083 | 11/1962 | Obitts | 294/1.2 X |
| 3,177,874 | 4/1965 | Spriggs | 294/1.2 |
| 4,026,591 | 5/1977 | Cleaveland | 294/1.2 |
| 4,037,866 | 7/1977 | Price | 294/1.2 |
| 4,097,081 | 6/1978 | England | 294/1.2 |
| 4,113,297 | 9/1978 | Quinn | 294/1.2 |
| 4,387,921 | 6/1983 | Licata | 294/1.2 |
| 4,784,258 | 11/1988 | Figari | 206/5.1 |
| 5,099,987 | 3/1992 | Bieri | 206/5.1 |

*Primary Examiner*—Russell D. Stormer
*Assistant Examiner*—Dean J. Kramer
*Attorney, Agent, or Firm*—James E. Wetterling

[57] ABSTRACT

An applicator assembly comprising a base having a handle portion and a support portion and including an applicator movably mounted or connected to the base and selectively positionable between an outwardly extending operative position wherein the lens is transferred to the eyeball, and a stored position wherein the contact lens is removably secured to the applicator and is also capable of being positioned for proper cleaning of the inside surface immediately prior to the application to the eyeball. A container is also provided for storing of the assembly wherein the cover or lid portion thereof is an eyepiece having a magnifying lens for properly viewing the contact lens when mounted on the subject applicator device for proper orientation of the lens immediately prior to placing on the eyeball.

17 Claims, 2 Drawing Sheets

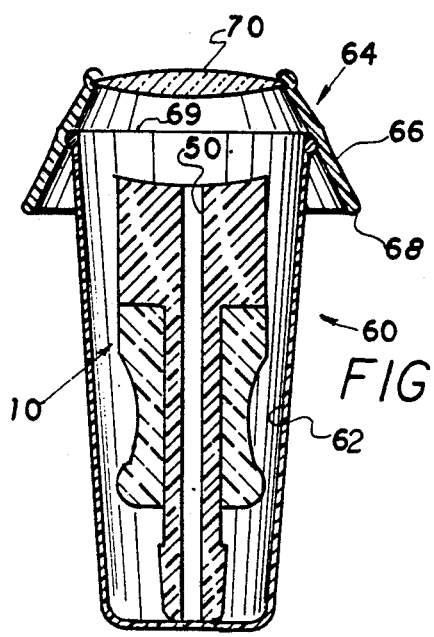
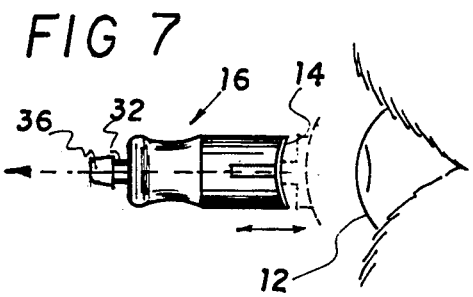
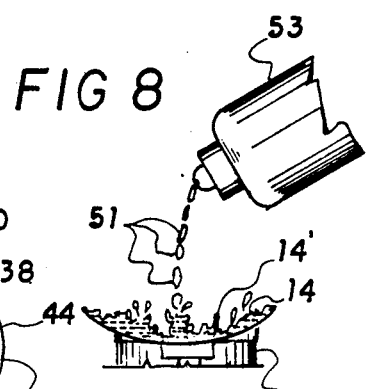
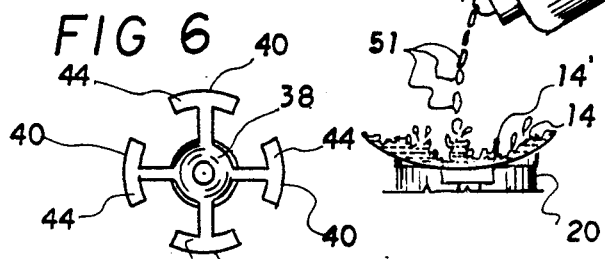
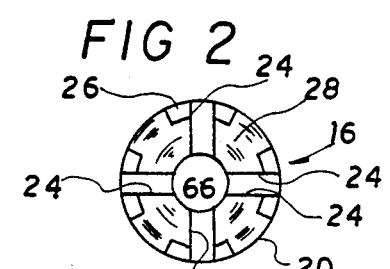
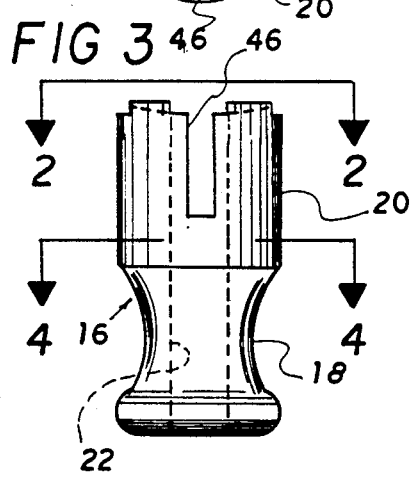
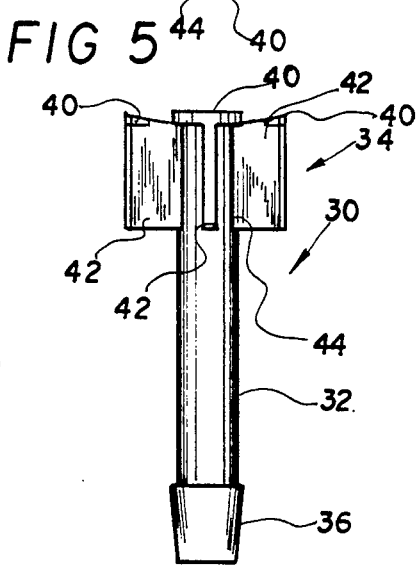
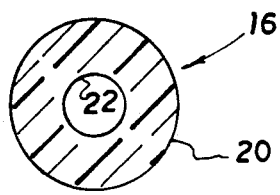

APPLICATOR DEVICE FOR POSITIONING A CONTACT LENS ON THE HUMAN EYE

BACKGROUND OF THE INVENTION

1. Field of the Invention

This invention relates to an applicator device for efficiently and accurately placing a contact lens on the outer surface of the human eye wherein the device is also capable of supporting the lens for proper and efficient cleaning immediately prior to application of the lens to the eyeball.

2. Description of the Prior Art

In modern day society many people with poor eyesight now utilize the wearing of contact lens to improve such eyesight rather than conventional spectacles or eye glasses. Advancements in the development and production of contact lens has increased the number of people who can actually wear the lens and also extended the amount of time such lenses can be worn. The improvement in contact lens technology has of course made available to wearer's of such lenses both the hard lens which was first developed and now the "soft" material lens which presents less aggravation to the eye and can be worn for extended periods However regardless of the type of contact utilized there is still the recognized problem of properly applying the contact lens to the eyeball. Conventional practice, in the past has lead to the precarious positioning of the contact lens on one finger of the user and the attempted but haphazard positioning of the lens in proper engagement with the exterior surface of the eyeball. Such a method is not only less than totally effective but frequently results in dropped lenses or inaccurate positioning particularly when the contact lens must be properly oriented immediately prior to application to the exterior surface of the eyeball.

As evidence of the fact that this problem has been recognized, the following United States Patents are representative of various devices which are directed to the application of a contact lens.

The U.S. Pat. No. 3,177,874 to Spriggs discloses a contact lens applicator which has a plurality of gear mechanisms which, when properly manipulated will properly activate a head formed of three upwardly extending prongs effectively arranged in a circle and having a somewhat of a flare type configuration so that the tips of these prongs are located in a manner to appropriately contact and grip the contact lens being applied. Gripping the lens occurs by water surface tension. This structure, while appearing to be applicable incorporated numerous mechanical linkage, in the form of gears, which therefore appears to be extremely complicated and therefore effects the operable life as well as the maintenance characteristics of this device.

The Patent to England, 4,097,081 discloses a device for inserting and removing contact lenses comprising an elongated resilient cylindrical body of small diameter having in its forward end a contact lens holding suction cup. A small diameter duct extends entirely through the body which is opened at its forward end and at its opposite end. The squeezing of the body of the device exerts a negative force or suction on a contact lens which is mounted on the holding suction cup. Further manipulation serves to release the lens in its proper location.

The Patent to Richmond, 3,134,208 discloses a lens holding device or more specifically an optical blank holding device utilized for the making of lenses rather than being specifically structured and designed to facilitate the application of such contact lenses to the eye in an efficient and accurate manner.

Of secondary interest is the Patent to Obits 3,063,083 which is directed to washing or cleansing devices and particularly to a kit for the washing and storing of contact lenses. The device does not specifically relate to a device which serves to properly apply and or position contact lens on the exterior surface of the eye in the conventional and accepted fashion.

The above referenced patents indicate that prior art has made numerous attempts to solve the well recognized problem of accurately and properly positioning the contact lens on the human eye. However, lack of commercial availability of devices such as this may be an indication that this well recognized problem is not solved by such devices. Therefore, there is total recognized need in this area for an applicator assembly which effectively and efficiently positions a contact lens on the human eye in a proper orientation and location. Such a preferred device should be capable of removably mounting the contact lens on the preferred applicator in a secure manner so as to eliminate any possibility of inadvertent dislodgment and possible loss of the lens while at the same time supporting or engaging the contact lens in a manner which allows easy transfer of the lens to the outer surface of the eyeball once the applicator is operatively positioned.

SUMMARY OF THE INVENTION

This invention relates to an applicator device which serves to efficiently, effectively and accurately place a contact lens on the exterior surface of the human eye. More specifically the subject applicator assembly comprises a base and a movably mounted applicator member thereon. The base includes a handle portion and a support portion preferably formed of a single, integral, one piece construction. A first channel is centrally and coaxially formed in the base and extends along the length thereof and completely therethrough. Such first channel is open at both ends and the channel is specifically dimensioned and structurally adapted to receive the applicator member.

The applicator member includes a holding means secured to and or defining one end of the applicator. The remainder of the applicator is defined by an elongated stem portion having an exterior transverse dimension sufficient to be mounted on the interior of the first channel and at the same time allow selective sliding movement of the length of the stem within the first channel. This allows the selective positioning of the applicator between a stored position and an operative position.

The holding means is specifically designed to removably mount a contact lens thereon by removable but relatively secure engagement with the exterior surface of the contact lens. This is accomplished through the provision of a plurality of outwardly extending lands which engage the exterior lens surface. Due to water surface tension between the moistened lens and the confronting surface of the lands, there is sufficient adhering force or pressure to removably secure the contact lens to the plurality of lands of the holding means. This provides proper positioning of the lens and also to allow its cleaning. Such cleaning technique of the contact lens when it engages the holding means and the support portion of the base is accomplished by the addition of a saline solution and will be described in greater detail hereinafter. The lands are further adapted collectively define a mounting surface for the engagement of the exterior surface of the contact lens as explained above.

The support portion of the base has a support surface formed on and defining the outer extremity of the support portion. The specific structural configuration of the holding means on the applicator member is adapted to effectively mate with the support portion on the base to the extent that the mounting surface on the holding means is positionable into flush engagement with the support surface on the support portion of the base when the applicator is selectively disposed into the aforementioned stored position. Once in such stored position the contact lens is wetted and mounted on the now flush support surface and mounting surface. As set forth above the adhering force is result of water surface tension between confronting or contacting surfaces of the lens and the support surface and mounting surfaces on the support portion of the base and the holding means respectively. It should also be emphasized that when in a stored position more surface area contacts the exterior surface of the contact lens. Accordingly more adhering force is developed and the contact lens is more stable when both the support surface and the mounting surface concurrently engages the outer surface of the contact lens. This is due to the fact that greater water surface tension exists. Such adhering force is caused by water surface tension as explained in detail herein and is sufficient to maintain secure engagement even when the lens is positioned in any of a variety of attitudes or orientations. Gravity will not dislodge the contact lens from its mounted position. Once the contact lens is properly cleaned and it is desired to place the contact lens on the eyeball, the applicator is movable in to the operative position. This operative position is defined by an outer spaced extension of the holding means and more specifically a separation of the mounting surface defined by the plurality of lands from the support surface of the base support portion. The exterior surface of the contact lens thereby breaks engagement with the support surface of the support portion of the base and therefore has less adhering force exerted thereon because less surface area is in actual engagement with the lens. The lens, is still maintained securely but removably on the mounting surface as the holding means and plurality of lands move outwardly from the support portion of the base and into the aforementioned outer extension, in spaced relation from the support portion of the base.

A second channel extends completely through the length of the elongated stem and holding means and is coaxially located relative to a central longitudinal axis which extends through the stem and therefore through the holding means. This second channel is open at both ends and is sufficiently large in dimension to allow light to pass therethrough from the outermost exterior end through the inner end adjacent to which the contact lens is mounted. The light will of course pass through the transparent contact lens. Such light can be easily viewed by the eyeball about to receive the contact lens. This light passing through the second channel is accurately aligned with the contact lens center such that continued viewing by the eyeball with the light passing through the second channel will serve as a sighting and or alignment means to accurately position the contact lens until it physically engages the exterior surface of the eyeball. Once such engagement or contact occurs the regular force exerted on the interior surface of the contact lens through its engagement with the exterior surface of the eyeball will be greater than the force serving to connect or mount the exterior surface of the contact lens to the mounting surface defined by the radially outwardly positioned lens. The contact lens will of course therefore be maintained on the exterior surface of the eyeball once the applicator is removed or selectively positioned back into the aforementioned stored position.

The present invention also includes a container structure which is capable of storage and containment of the applicator assembly therein. An additional feature of this container will be that the cover thereof is structured to define an eye piece which includes a magnifying lens. The eye piece can be fitted over one of the eyes of the user and is used to properly sight and magnify the position of the contact lens on the applicator assembly. Such magnified viewing allows the proper orientation of the lens relative to the applicator so that when it engages the exterior surface of the eyeball it is properly oriented relative thereto.

BRIEF DESCRIPTION OF THE DRAWINGS

For a fuller understanding of the nature of the present invention, reference is had to the following detailed description taken in connection with the accompanying drawings in which:

FIG. 1 is a longitudinal sectional view of the applicator assembly stored within a container.

FIG. 2 is an end view of a component of the embodiment of FIG. 3 along line 2—2 thereof.

FIG. 3 is a front view of one component of the applicator assembly off the present invention.

FIG. 4 is a sectional view taken along line 4—4 of FIG. 3.

FIG. 5 is a front view of a cooperative component of the applicator assembly of the present invention.

FIG. 6 is an end view FIG. 5.

FIG. 7 is a side view showing the two components of FIGS. 3 and 5 in intended connection with one another and relationship thereof to the eyeball on which the contact lens is to be placed.

FIG. 8 is a front view in partial cut-away showing a cleansing method usable with the applicator assembly of the present invention.

Like reference numerals refer to like parts throughout the several views of the drawings.

DETAILED DESCRIPTION OF THE PREFERRED EMBODIMENT

Figure 9:
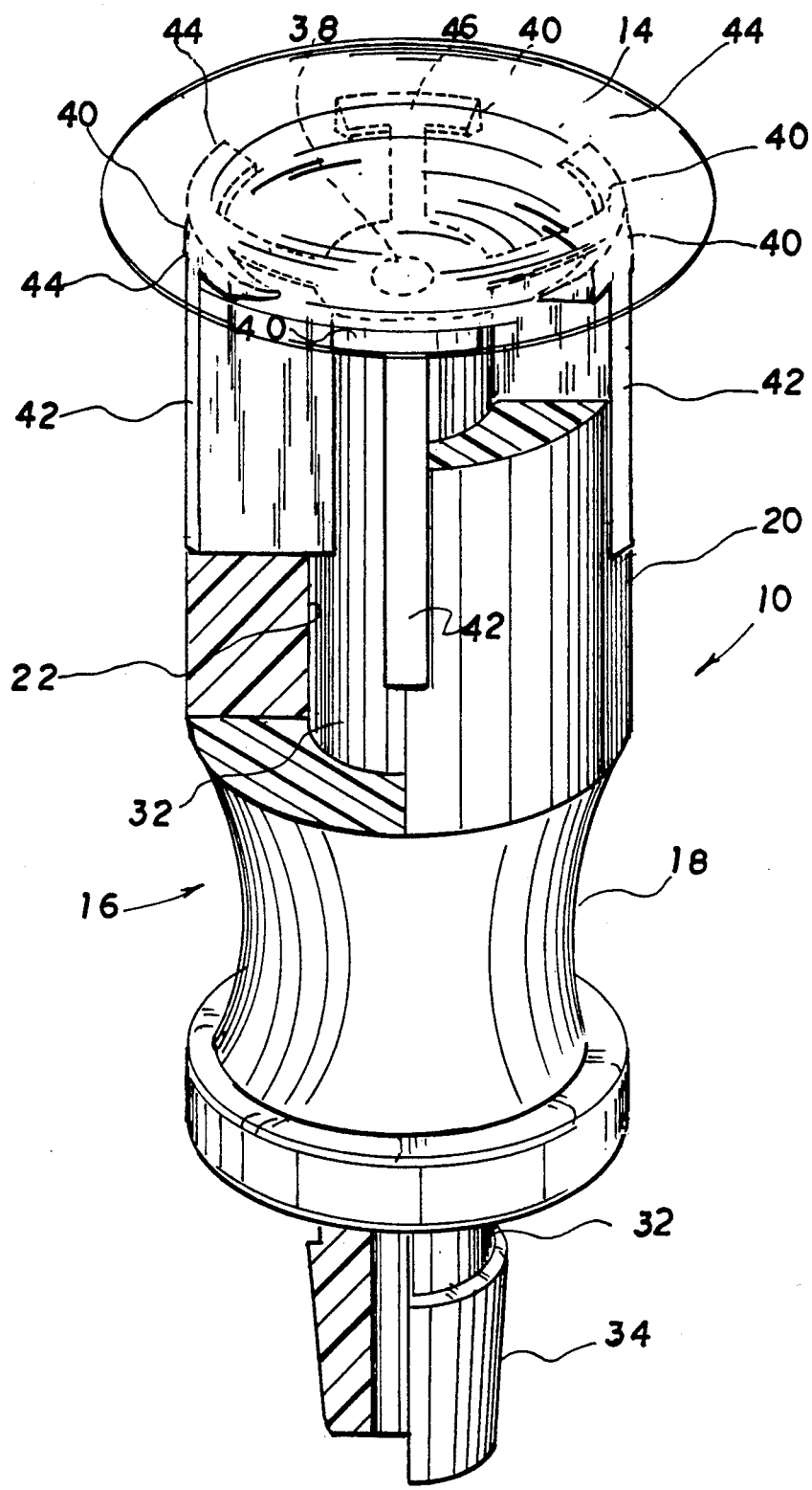
FIG. 9 is a perspective view in partial section and cut away showing mating engagement of the two components of the subject applicator assembly with a contact lens mounted thereon.

As shown in the accompanying figures the present invention is directed towards an applicator assembly generally indicated as 10 designed to apply a contact lens to the eyeball 12 of a user's eye. The contact lens 14 is mounted in the position best shown in FIG. 9 for purposes of cleansing as will be explained in greater detail specifically with reference to FIG. 8 and also in such position for purposes of application as best shown in FIGS. 7 and 9. It should be noted that while the contact lens is represented in relative dimension and configuration as shown in FIG. 9 such contact lens, utilizing the preferred applicator assembly of the present invention may take a variety of dimensions and configurations, all of which contact lenses are now commercially available.

The subject applicator assembly includes a base generally indicated as 16 and shown in detail in FIGS. 2, 3 and 4. The base 16 includes a handle portion 18 configured to be effectively gripped by the hands or more specifically the fingers of the user and a support portion 20. The base 16 also includes a first channel 22 extending completely through the length of the base and disposed in substantially coaxial alignment with a central longitudinal axis (not demonstrated for purposes of clarity). Also, the first central channel 22 is open at both ends and is transversely dimensioned so as to slidingly receive therein an applicator member generally indicated as 30. The base 16 further comprises a plurality of elongated slots 24 and also a plurality of spaced apart recesses as at 26. The slots and the recesses are dimensioned and otherwise adapted and disposed to receive specific portions or components of the applicator member 30, as will be explained in greater detail hereinafter when such applicator member is disposed in a stored position as best shown in FIGS. 1 and 7. Further the support portion includes a support surface 28 which has a somewhat concave configuration so as to be readily adaptable to the convex configuration of the exterior surface of the contact lens 14 when such contact lens is mounted thereon.

The applicator assembly, as said forth above, further includes an applicator 30 having an elongated stem 32 with a holding means generally indicated as 34 affixed to and at least partially defining one end thereof. The opposite end of the stem 32 includes a fixedly or integrally attached stop member 36. The outer transverse dimension of the stem 32 is such as to be slidingly received within the first channel 22 of the base 16. Therefore it should be apparent that the applicator 30 is selectively positionable by the hands of the user between a stored position (See FIGS. 1 and 7) and an operative position as best shown in FIG. 9. The stop member 36 is provided so as to prevent inadvertent removal or displacement of the stem 32 from passing out of the central channel 22 of the base 16. It should be apparent therefore that the transverse dimension of the stop member 36 is at least somewhat greater than the inner transverse dimension of the channel 22.

The holding means 34 includes a head portion as at 38 and a plurality of radially outward extending lands 40 which may be disposed in spaced relation to one another or otherwise interconnected. Connecting means in the form of spaced apart flange like fingers 42 are directed radially outward from the head 38 and are connected at the upper and outermost extremity to the lands 40. Such flange like finger members 42 have their inner most longitudinal end as at 44 connected or integrally formed on the exterior surface of the stem. The lands are collectively shaped to define a somewhat concave surface and they are disposed to collectively define what may be referred to as a mounting surface which engages and supports the exterior surface of the contact lens 14 as best shown in FIG. 9.

The aforementioned operative position is defined by the holding means 34 and particularly the lands 40 and the head portion 38 extending outwardly away from the support portion 20 and particularly the support surface 28 of the base 16. In such a position the stem is manipulated to accomplish such outer positioning wherein the contact lens 14 is mounted on and thereby supported exclusively by the lands 40 and in particular the mounting surface 44 collectively defined by the exterior surface of at least the lens and depending upon the shape of a contact lens, the exposed surfaces of the fingers 42.

When in the aforementioned stored position the mounting surface 44 defined by the exterior, exposed surface collectively of the plurality of lands 40 is disposed in flush engagement with the support surface 28 of the support portion 20 of the base 16. This is accomplished by a mating engagement of the flange like fingers 42 within one of a plurality of spaced apart elongated slots 24 disposed in spaced apart relation to one another and integrally formed in the support portion 20 as said forth above. Similarly, a plurality of spaced apart recesses 26 are dimensioned, configured and otherwise structurally adapted to receive the lands 40 therein. The relative dimension and configuration of the recesses 26 and the lands 40 are such as to dispose the mounting surface 44 into flush relation with the support surface 28 to define an overall somewhat concave configuration when such flush engagement between these two surfaces exists. In such a stored position and when the above noted surfaces are in flush relation to one another the contact lens 14 is placed thereon. An adhering force created by water surface tension or force is exerted on the exterior surface of the contact lens 14 thereby securely but removably holding the contact lens in an operative position and in engagement with both the mounting surfaces 44 of the lands and the support surface 28 of the support portion 20. However when it is desired to physically apply the contact lens 14 to the exterior surface of the eye ball 12, the stem 32 is manipulated relative to the base 16 in a manner which causes the outer extension of the holding means 34 from the support portion 20 of base 16 (See FIG. 9).

In the position shown in FIG. 7 the assembly is still in its stored position. However when it is desired to physically apply the lens the holding means 34 and particularly the lands 40 extend outwardly in spaced relation from the support portion 20, this causes the mounting surface of the lands 40 to clearly separate in an outer spaced extension from the support surface 28 and support portion 20 (See dotted lines of FIG. 7 and the details of FIG. 9). It is important to note, and as set forth above in somewhat detail, the adhering force due to the existence of water surface tension is somewhat less when the device is in the outer spaced position since a smaller surface area, namely the surface area of the mounting surfaces of the lands 40 "(and possibly the exposed surfaces of fingers 42)" are only in contact with the outer surface of the contact lens. A greater adhering force due to engagement of a greater surface area exists between the lens when in fact both the mounting surfaces 44 of the lands and the support surface 28 of the support portion 20 are in flush engagement and when both engage the outer surface of the contact lens.

It is important to note that the stem 32 as well as the holding means 34 includes a second elongated channel extending completely there through and being open at both ends. This channel 50 is disposed in coaxially alignment with a central longitudinal axis of the stem 32. The transverse dimension of the second channel 50 is such as to allow light to pass therethrough. This light may be viewed as it passes through the contact lens 14 by the eyeball 12 immediately prior to the application or physical contact of the lens 14 to the exterior surface of the eyeball 12. The continuous viewing by the eyeball of the light passing through the second elongated channel 50 and through the transparent contact lens will serve to automatically align and therefore properly position the contact lens as it approaches, eventually contacts and is transferred onto the outer surface of the eyeball 12.

Another feature of the present invention is shown in FIG. 8. When the lens 14 is mounted on both the lands 40 and the support portion 20 when the applicator 30 and the base 16 are in the aforementioned stored position, a cleansing fluid may be applied directly to the inner surface 14' of the contact lens 14. Cleansing is readily accomplished. The plurality of drops as at 51 are allowed to pass through a certain distance, which may of course vary, but which is preferably outward to six inches above the inner surface 14' when in the orientational position shown in FIG. 8. Such drops may pass from the conventional container in which such cleansing solutions are sold as at 53. The splashing of the individual drops 51 onto the inner surface 14' will cause them to "bounce" or "ricochet" off such inner surface and carry with them T when passing from the inner surface 14', any debris or dust which would have a tendency to irritate the eyeball. The greater adhering force between the contact lens 14 and the now combined, flush support surface 28 and mounting surfaces 44 of the lands 40 will maintain the contact lens 14 in its secured position as shown in FIG. 8 even under the pressure exerted thereon by the cleansing drops 51 falling from a significant height or distance. After cleansing the stem 32 is manipulated until the holding means 34 and particularly the lands 40 are disposed in the aforementioned operative position immediately prior to contact between the lens 14 and the eyeball 12. The adhering force on the lens is thereby reduced.

Yet another feature of the present invention is the provision of a container generally indicated as 60. The container includes a substantially hollow interior 62 dimensionally configured to receive and have stored therein the assembly 10 preferably when in its stored position. The container 60 includes a cover portion generally indicated as 64 which may more specifically be defined by an eye piece. The eye piece includes an outwardly flared surrounding peripheral wall as at 66 having the exterior peripheral rim as at 68 dimensioned to fit over but received in overlying relation to an eyeball of the user. The cover structure 64 also includes the existence of a magnifying lens 70. When the cover is properly positioned over the eyeball viewing through the magnifying lens 70 will allow enhanced observation of the contact lens. The contact lens 14 can thereby be properly oriented by the hands or fingers of the user until it is accurately positioned so as to accomplish proper placement in covering relation to the eyeball 12. Proper placement and actual contact of the lens 14 occurs as shown in FIG. 7 when the line of sight of the eyeball 12 passes through the elongated second channel 50 by constantly viewing the light.

The cover 64 is removably attached in overlying, covering relation to the open end or mouth 69 of the container 60 as shown.

Now that the invention has been described:
What is claimed is:
1. An applicator assembly for a contact lens, for a human eye, said assembly comprising:
 a) a base including a handle portion and a support portion connected to said handle portion,
 b) an applicator movably mounted on said base and positioned between a stored position and an operative position,
 c) said applicator comprising holding means adapted for removably holding a contact lens thereon, said holding means comprising a head portion and a plurality of lands extending radially outward from said head portion, said plurality of lands each including an exposed exterior surface and collectively defining a mounting surface for a contact lens,
 d) said applicator further comprising positioning means connected to said holding means and movable therewith relative to said base between said stored position and said operative position,
 e) said operative position defined by said holding means extending outwardly in spaced relation from said support portion,
 f) said stored position defined by a mating engagement between said holding mean sand said support portion, and said base further including a support surface formed on an outer extremity of said support portion, said support surface dimensioned and adapted to removably support a contact lens thereon when said applicator is disposed in said stored position.

2. An assembly as in claim 1 wherein said base comprises an elongated first channel extending therethrough and being open at both of two opposite ends, said first channel transversely dimensioned to slidingly receive said holding means therein.

3. An assembly as in claim 2 wherein said holding means comprises an elongated stem having a sufficient longitudinal dimension to extend outwardly from at least one of said opposite ends when in either said operative or said stored position.

4. An assembly as in claim 3 wherein said stem includes said holding means fixedly secured to one end thereof and an opposite end thereof including a stop member each having a sufficiently larger dimension than said first channel to restrict passage of either therethrough.

5. As assembly as in claim 3 wherein said stem includes an elongated second channel extending through the length of said stem and said holding means in coaxial relation to a central longitudinal axis thereof, said second channel disposed and adapted to operatively align the holding means with an eyeball for placement of a contact lens thereon when said holding means is in said operative position.

6. An assembly as in claim 1 wherein said lands are configured and adapted to orient said mounting surface in flush engagement with said support surface when said applicator is in said stored position.

7. An assembly as in claim 6 wherein said support surface and said mounting surface collectively define a substantially concave configuration when said applicator is in said stored position.

8. An assembly as in claim 6 wherein said operative position is further defined by an outer, spaced extension of said head portion and said plurality of lands from said support portion and said plurality of lands and said mounting surface removably engaging an outer surface of the contact lens.

9. An assembly as in claim 6 further comprising connecting means adapted for securing said plurality of lands in an outwardly spaced relation to said head portion and fixedly secured to both said head portion and said plurality of lands.

10. An assembly as in claim 9 wherein said connecting means comprises a plurality of fingers each having an inner end fixedly secured to said stem and extending radially outward from said stem and said head portions and having an outer end thereof secured to one of a plurality of lands.

11. An assembly as in claim 10 wherein each of said lands extends outwardly from both longitudinal sides of a corresponding finger in transverse relation thereto.

12. An assembly as in claim 11 wherein said support portion comprises a plurality of slots formed therein in spaced relation to one another and each being disposed and configured to removably receive one of said fingers' therein when said applicator is in a stored position.

13. An assembly as in claim 12 wherein said support portion further comprises a plurality of recesses formed therein and each dimensioned and adapted to receive one of said plurality of lands therein when said applicator is in said stored position.

14. An assembly as in claim 13 wherein said plurality of slots and recesses are dimensioned and configured to position said mounting surface in flush relation to said support surface when said fingers and said lands are respectively positioned therein.

15. An assembly as in claim 1 further comprising in combination a container means structurally adapted for removably containing said base and said applicator when movably connected together.

16. An assembly as in claim 15 wherein said container means comprises a hollow interior container body and a cover portion connected in removably covering relation to said container body.

17. An assembly as in claim 16 wherein said cover portion comprises an eye piece including a magnifying lens structurally adapted for magnified viewing of the contact lens when mounted on said applicator or support portion of said base.

* * * * *